(12) United States Patent
Hernandez

(10) Patent No.: US 12,390,445 B2
(45) Date of Patent: Aug. 19, 2025

(54) BOTANICAL CALMING COMPOSITION

(71) Applicant: Topix Pharmaceuticals, Inc., N. Amityville, NY (US)

(72) Inventor: Steven Hernandez, Blue Point, NY (US)

(73) Assignee: Topix Pharmaceuticals, Inc., N. Amityville, NY (US)

( * ) Notice: Subject to any disclaimer, the term of this patent is extended or adjusted under 35 U.S.C. 154(b) by 252 days.

(21) Appl. No.: 18/096,796

(22) Filed: Jan. 13, 2023

(65) Prior Publication Data

US 2023/0277498 A1   Sep. 7, 2023

Related U.S. Application Data

(60) Provisional application No. 63/299,209, filed on Jan. 13, 2022.

(51) Int. Cl.

| | | |
|---|---|---|
| *A61K 31/375* | (2006.01) | |
| *A61K 8/19* | (2006.01) | |
| *A61K 8/362* | (2006.01) | |
| *A61K 8/67* | (2006.01) | |
| *A61K 8/92* | (2006.01) | |
| *A61K 8/9789* | (2017.01) | |
| *A61K 31/20* | (2006.01) | |
| *A61K 33/34* | (2006.01) | |
| *A61K 36/185* | (2006.01) | |
| *A61Q 19/08* | (2006.01) | |

(52) U.S. Cl.
CPC .............. *A61K 31/375* (2013.01); *A61K 8/19* (2013.01); *A61K 8/362* (2013.01); *A61K 8/676* (2013.01); *A61K 8/922* (2013.01); *A61K 8/9789* (2017.08); *A61K 31/20* (2013.01); *A61K 33/34* (2013.01); *A61K 36/185* (2013.01); *A61Q 19/08* (2013.01); *A61K 2800/592* (2013.01)

(58) Field of Classification Search
CPC .......... A61K 8/362; A61K 8/34; A61K 47/02; A61K 31/20; A61K 31/245; A61K 36/61
See application file for complete search history.

(56) References Cited

U.S. PATENT DOCUMENTS

| | | | |
|---|---|---|---|
| 2004/0086471 A1 | 5/2004 | Lin et al. | |
| 2010/0278759 A1* | 11/2010 | Murad | A61K 47/02 424/59 |
| 2014/0037772 A1* | 2/2014 | Lien | A61K 8/362 |
| 2014/0066837 A1 | 3/2014 | Moy | |
| 2015/0080329 A1* | 3/2015 | Manku | A61K 31/7036 |
| 2015/0086494 A1* | 3/2015 | Sekura | A61K 31/245 |
| 2016/0243057 A1 | 8/2016 | McWherter et al. | |
| 2020/0215116 A1 | 7/2020 | Wootten | |
| 2021/0169759 A1 | 6/2021 | Mullen et al. | |

OTHER PUBLICATIONS

PCT International Search Report and Written Opinion for International Application No. PCT/US2023/010762, mailed Apr. 25, 2023, 25 pages.

* cited by examiner

*Primary Examiner* — Robert A Wax
*Assistant Examiner* — Kimberly Barber
(74) *Attorney, Agent, or Firm* — Lowenstein Sandler LLP

(57) ABSTRACT

Disclosed herein is a topical composition that delivers advanced environmental protection to the skin, brightens the complexion of the skin, and delivers anti-aging benefits to the skin. The topical composition includes a vitamin C source, a copper source, one or more cannabinoid components, and sodium hyaluronate. Also disclosed herein are methods of administering the topical compositions.

18 Claims, No Drawings

BOTANICAL CALMING COMPOSITION

CROSS REFERENCE TO RELATED APPLICATION(S)

The present invention claims priority to U.S. Provisional Patent Application No. 63/299,209 filed on Jan. 13, 2022, the entire contents of which are incorporated herein in its entirety.

FIELD OF THE INVENTION

The present invention relates to cosmetic compositions for skin care applications.

BACKGROUND OF THE INVENTION

Overexposure to the sun and other toxic free radical sources and irritants induces skin damage, resulting in a variety of disfiguring skin conditions. Among these skin conditions, wrinkles, fine lines, loss of elasticity, sagging, dryness, age spots are caused by sun damage and aging. Wrinkles of the skin are either deep furrows and creases or fine lines. Wrinkles can occur on any part of the body, but especially where sun exposure is greatest, such as on the face, neck, forearms and hands.

Free radicals from ultraviolet light (UV) are known to increase with air pollution in areas of concentrated populations, thereby magnifying the problem. The free radicals are destructive in that the free radicals hydrolyze elastin fibers in the skin and desynthesize collagen in the lower dermal layers of the skin, thereby causing skin wrinkles and other damaging skin conditions.

Nowadays, individuals often seek means for preventing and/or counteracting effects of aging and sun exposure. A variety of cosmetic compositions as well as homeopathic remedies are available to the consumer looking achieve a more youthful and healthy appearance. However, there remains a need for topical compositions that provide effective treatment and preventative measures against skin photo-aging and related skin disorders.

SUMMARY

It is an object of certain embodiments of the disclosure to provide a topical composition, a method of preparing, and a method of using said topical composition for protecting the skin against extrinsic and intrinsic aggressors which may degrade the skin's youthful appearance.

The term "administering the topical composition" as used herein refers to applying topically onto a skin of a subject, e.g., on the face, neck, hands, feet, elbows, knees, and the like. As used herein, the terms "application," "apply," and "applying" with respect to a disclosed topical formulation or method of using a disclosed topical formulation, refer to any manner of administering a topical formulation to the skin, for example, the skin of a person, such as the skin of a patient, which, in medical or cosmetology practice, delivers the formulation to the subject's skin surface. Smearing, rubbing, spreading, spraying a disclosed topical formulation, with or without the aid of suitable devices, on a subject's skin are all included within the scope of the term "application," as used herein. The term "topical" or "topically" with respect to administration or application of a disclosed skincare formulation refers to epicutaneous administration or application, onto skin. The application can be manually (e.g., directly with the hands) or manipulated with an applicator, cloth, device, roll-on, wipes, unit dose sponge applicators, liquid applied with swabs or cotton balls, impregnated gauze or other substrates, coated silicone sheets or other sheet goods, coated bandages or externally fixed devices, towelettes, individually packaged pledgettes, transdermal delivery system, etc. Administration can be self-administration or administration by a medical professional or caregiver.

In one embodiment of the present invention, a topical composition comprises a vitamin C source, a copper source, one or more cannabinoid components, and sodium hyaluronate. In another embodiment, the topical composition may include two or more of a vitamin C source, a copper source, one or more cannabinoid components, or sodium hyaluronate. In another embodiment, the topical composition may include three or more of a vitamin C source, a copper source, one or more cannabinoid components or sodium hyaluronate.

In certain embodiments of the topical composition, the vitamin C source includes ascorbic acid, tetrahexyldecyl ascorbate, or a combination thereof.

In certain embodiments of the topical composition, the copper source comprises copper PCA (pyrrolidone carboxylic acid), copper peptide, or a combination thereof.

In certain embodiments of the topical composition, the one or more cannabinoid component includes hemp oil, purified cannabinoid, hemp seed oil, or a combination thereof.

In one embodiment, the topical composition further includes an azelaic acid source. The azelaic acid source may include azeloglicina.

In certain embodiments, the topical composition further includes an adaptogen source. The adaptogen source includes Resurgent Power BCR.

In certain embodiments, the topical composition further includes an antioxidant system comprising green tea polyphenols.

In some embodiments, the topical composition further includes one or more of a solvent, a thickener, a chelating agent, vitamin D, a solubilizer, melatonin, preservative, one or more botanical extracts, a colorant, or a combination thereof. In certain embodiments, the topical composition may include a solvent comprising water, glycerin, or a combination thereof. In certain embodiments, the topical composition may include a thickener comprising a cellulosic thickener, a synthetic polymer thickener, or a combination thereof. In certain embodiments, the topical composition may include a solubilizer having an HLB greater than 6, preferably an HLB greater than 12. In certain embodiments, the topical composition may include one or more botanical extracts selected from thyme herb, mulberry extract, willow bark extract, elderberry, *Echinacea*, cucumber base extract, or a combination thereof.

In certain embodiments, the topical composition may further include a plant-based growth factor. In certain embodiments, the plant-based growth factor may include a plant-based synthetic human epidermal growth factor (EGF), a plant-based synthetic vascular endothelial growth factor (VEGF), a plant-based synthetic transforming growth factor (TGF), a plant-based synthetic insulin growth factor (IGF), or a combination thereof.

In certain embodiments of the topical composition, the vitamin C source may be included in an amount from about 0.001 wt. % to about 20 wt. %, from about 0.05 wt. % to about 10 wt. %, from about 0.1 wt. % to about 5 wt. %, or from about 1 wt. % to about 2.5 wt. % based on a total weight of the topical composition.

In certain embodiments of the topical composition, the copper source may be included in an amount from about 0.001 wt. % to about 5 wt. %, from about 0.05 wt. % to about 4 wt. %, from about 0.1 wt. % to about 3 wt. %, or from about 1 wt. % to about 2.5 wt. % based on a total weight of the topical composition.

In some embodiments of the topical composition, the one or more cannabinoid component may be hemp oil. In some embodiments, the hemp oil may be included in an amount from about 0.001 wt. % to about 10 wt. %, about 0.05 wt. % to about 5 wt. %, about 0.1 wt. % to about 5 wt. %, or about 1 wt. % to about 2.5 wt. % based on a total weight of the topical composition.

In some embodiments of the topical composition, the one or more cannabinoid component may be purified cannabinoid. In some embodiments of the topical composition, purified cannabinoid may be included in an amount from about 0.0001 wt. % to about 5 wt. %, from about 0.001 wt. % to about 4 wt. %, from about 0.01 wt. % to about 3 wt. %, from about 0.1 wt. % to about 2.5 wt. %, or from about 1 wt. % to about 1.75 wt. % based on a total weight of the topical composition.

In some embodiments of the topical composition, the one or more cannabinoid component may be hemp seed oil. In some embodiments, the hemp seed oil may be included in an amount from about 0.001 wt. % to about 10 wt. %, about 0.05 wt. % to about 5 wt. %, about 0.1 wt. % to about 5 wt. %, or about 1 wt. % to about 2.5 wt. % based on a total weight of the topical composition.

In some embodiments of the topical composition, sodium hyaluronate may be included in an amount from about 0.1 wt. % to about 5 wt. %, about 1 wt. % to about 4 wt. %, or about 2 wt. % to about 3 wt. % based on a total weight of the topical composition.

In some embodiments of the topical composition, the thickener may be included in an amount from about 0 wt. % to about 3 wt. %, about 0.5 wt. % to about 2.5 wt. %, or about 1 wt. % to about 2 wt. % based on a total weight of the topical composition.

In some embodiments of the topical composition, the solubilizer may be included in an amount from about 0 wt. % to about 10 wt. %, about 1 wt. % to about 9 wt. %, about 2 wt. % to about 8 wt. %, about 3 wt. % to about 7 wt. %, or about 4 wt. % to about 6 wt. % based on a total weight of the topical composition.

In some embodiments of the topical composition, the one or more botanical extracts may be thyme herb. In some embodiments, the thyme herb may be included in an amount from about 0 wt. % to about 10 wt. %, about 1 wt. % to about 9 wt. %, about 2 wt. % to about 8 wt. %, about 3 wt. % to about 7 wt. %, or about 4 wt. % to about 6 wt. % based on a total weight of the topical composition.

In some embodiments of the topical composition, the one or more botanical extracts may be mulberry extract. In some embodiments, the mulberry extract may be included in an amount from about 0 wt. % to about 10 wt. %, about 1 wt. % to about 9 wt. %, about 2 wt. % to about 8 wt. %, about 3 wt. % to about 7 wt. %, or about 4 wt. % to about 6 wt. % based on a total weight of the topical composition.

In some embodiments of the topical composition, the one or more botanical extracts may be elderberry. In some embodiments, the elderberry may be included in an amount from about 0 wt. % to about 10 wt. %, about 1 wt. % to about 9 wt. %, about 2 wt. % to about 8 wt. %, about 3 wt. % to about 7 wt. %, or about 4 wt. % to about 6 wt. % based on a total weight of the topical composition.

In some embodiments of the topical composition, the one or more botanical extracts may be willow bark extract. In some embodiments, the willow bark extract may be included in an amount from about 0 wt. % to about 10 wt. %, about 1 wt. % to about 9 wt. %, about 2 wt. % to about 8 wt. %, about 3 wt. % to about 7 wt. %, or about 4 wt. % to about 6 wt. % based on a total weight of the topical composition.

In some embodiments of the topical composition, the preservative may be phenoxyethanol. In some embodiments of the topical composition, the solvent may include glycerin and water. In some embodiments of the topical composition, glycerin may be included in an amount from about 0 wt. % to about 20 wt. %, about 1 wt. % to about 15 wt. %, about 2 wt. % to about 12 wt. %, about 3 wt. % to about 10 wt. %, 4 wt. % to about 8 wt. %, or about 5 wt. % to about 7 wt. % based on a total weight of the topical composition.

In certain embodiments of the topical composition, melatonin may be included in an amount from about 0.001 wt. % to about 2 wt. %, about 0.01 wt. % to about 1 wt. %, or about 0.1 wt. % to about 0.5 wt. % based on a total weight of the topical composition.

In certain embodiments, the topical composition further includes allantoin. In some embodiments, allantoin may be included in an amount from about 0 wt. % to about 2 wt. %, about 0.01 wt. % to about 1 wt. %, or about 0.1 wt. % to about 0.5 wt. % based on a total weight of the topical composition.

In certain embodiments, the topical composition further includes DL panthenol. In some embodiments, DL panthenol may be included in an amount from about 0 wt. % to about 5 wt. %, about 1 wt. % to about 4 wt. %, or about 2 wt. % to about 3 wt. % based on a total weight of the topical composition.

In certain embodiments, the topical composition further includes disodium EDTA. In some embodiments, disodium EDTA may be included in an amount from about 0 wt. % to about 1 wt. %, about 0.001 wt. % to about 0.9 wt. %, about 0.01 wt. % to about 0.75 wt. %, or about 0.1 wt. % to about 0.5 wt. % based on a total weight of the topical composition.

In certain embodiments, the topical composition further includes a plant-based growth factor. In some embodiments, the plant-based growth factor may be included in an amount from about 0.1 wt. % to about 10 wt. %, about 0.5 wt. % to about 9 wt. %, about 1 wt. % to about 8 wt. %, about 2 wt. % to about 7 wt. %, about 3 wt. % to about 6 wt. %, or about 4 wt. % to about 5 wt. %, based on a total weight of the topical composition.

In another embodiment, a method of treating skin includes administering to the skin a topical composition.

In certain embodiments, the instant disclosure is directed to a method of preparing any of the topical compositions described herein by combining an ascorbate component and above 0 wt % to about 1 wt % of an antioxidant system that includes green tea polyphenols.

DETAILED DESCRIPTION

The following definitions are used, unless otherwise described.

The term "alkyl" as used herein refers to straight and branched hydrocarbon groups. Reference to an individual radical such as propyl embraces only the straight chain radical, a branched chain isomer such as isopropyl being specifically referred to.

The term "halo" or "halogen" as used herein refers to fluoro, chloro, bromo and iodo.

The term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. ($C_3$-$C_7$) carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocyles having 7 to 12 carbon atoms as a bicycle, and up to about 20 carbon atoms as a polycycle. Multicyclic carbocyles can be connected to each other via a single carbon atom to form a spiro connection (e.g. spiropentane, spiro[4,5]decane, spiro[4.5]decane, etc.), via two adjacent carbon atoms to form a fused connection such as a bicyclo[4,5], [5,5], [5,6] or [6,6] system, or 9 or 10 ring atoms arranged as a bicyclo[5,6] or [6,6] system (e.g. decahydronaphthalene, norsabinane, norcarane) or via two non-adjacent carbon atoms to form a bridged connection (e.g. norbornane, bicyclo[2.2.2]octane, etc.). The "carbocycle" or "carbocyclyl" may also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl and cycloheptyl.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1,2,3,4-tetrahydronaphthyl, anthracenyl, and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

As used herein, "free or substantially free," refers to a topical composition that comprises less than about 1 wt %, less than about 0.5 wt %, less than about 0.25 wt %, less than about 0.1 wt %, less than about 0.05 wt %, less than about 0.01 wt %, or 0 wt % of said component.

As used herein, the term "plant-based synthetic" when referencing growth factors refers to a botanical plant that is bioengineering such that the botanical plant, or extract therefrom, functions as a growth factor.

Topical Composition

According to various embodiments, the present disclosure is related to a topical composition that includes a continuous phase and a dispersed phase. The topical composition includes an ascorbate component, a copper component and a cannabinoid component. In certain embodiments, the topical composition further includes at least one additional cosmetically acceptable excipient.

The ascorbate component in any of the topical compositions described herein can include ascorbic acid, or its derivatives, such as ascorbyl palmitate, sodium ascorbate, potassium ascorbate, ammonium ascorbate, triethanolamine ascorbate, ascorbyl phosphate or magnesium ascorbyl phosphate, ascorbic acid polypeptides, ascorbyl glucosamine, ascorbic acid polymers, esters of ascorbic acid, amides of ascorbic acid, L-ascorbic acid, tetrahexyldecyl ascorbate, known as vitamin C, or other derivatives, or related compounds, including botanical or herbal extracts, such as extracts of acerola, citrus extracts, strawberry, which may supply L-ascorbic acid or its derivatives. In certain embodiments, the ascorbate component in the topical composition includes ascorbic acid, tetrahexyldecyl ascorbate, or a combination thereof.

The ascorbate component in any of the topical compositions described herein may be present in a concentration of from any of about 0.001 wt %, 0.01 wt %, 0.1 wt %, about 1 wt %, about 5 wt %, about 10 wt %, to any of about 12 wt %, about 15 wt %, about 18%, or about 20 wt %, based on total weight of the topical composition. In certain embodiments, the ascorbate component is present in any of the topical compositions described herein in an amount ranging from about 0.001 wt % to about 20 wt %, from about 0.05 wt % to about 10 wt %, about 0.1 wt % to about 5 wt % or from about 1 wt % to about 2.5 wt %, based on total weight of the topical composition.

The copper component in any of the topical compositions described herein can include copper pyrrolidone carboxylic acid ("PCA"), copper peptide, or a combination thereof.

The copper component in any of the topical compositions described herein may be present in a concentration of from any of about 0.001 wt %, about 0.01 wt %, about 0.1 wt %, about 1 wt %, to any of about 2 wt %, about 2.5 wt %, about 3 wt %, about 4 wt %, about 5 wt %, based on total weight of the topical composition.

The cannabinoid component in any of the topical compositions described herein can include hemp oil, purified cannabinoid, hemp seed oil, cannabidiol, or a combination thereof.

In some embodiments, the cannabinoid component can include hemp oil. The hemp oil may be present in a concentration of from any of about 0.001 wt %, about 0.01 wt %, about 0.1 wt %, about 1 wt %, about 2.5 wt %, about 5 wt % to any of about 6 wt %, about 7 wt %, about 8 wt %, about 9 wt % or about 10 wt %, based on total weight of the topical composition.

In some embodiments, the cannabinoid component can include purified cannabinoid. The purified cannabinoid may be present in a concentration of from any of about 0.0001 wt %, about 0.001 wt %, about 0.01 wt %, about 0.1 wt %, 1 wt % to about 1.75 wt %, about 2.5 wt %, about 3 wt %, about 4 wt %, or about 5 wt %, based on total weight of the topical composition.

In some compositions, the cannabinoid component can include hemp seed oil. The hemp seed oil may be present in a concentration of from any of about 0.001 wt %, about 0.01 wt %, about 0.1 wt %, about 1 wt %, about 2.5 wt %, about 5 wt % to any of about 6 wt %, about 7 wt %, about 8 wt %, about 9 wt % or about 10 wt %, based on total weight of the topical composition.

The sodium hyaluronate in the topical composition may be present in a concentration of from any of about 0.1 wt %, about 1 wt %, or about 2 wt % to about 3 wt %, 4 wt % or 5 wt %, based on total weight of the topical composition. The sodium hyaluronate in the topical composition may also be present in a concentration greater than 0 to about 5 wt %.

Certain plant, such as green tea, that are composed of a high content of polyphenols which are bioflavonoids and have anti-oxidant properties are included in any of the topical compositions described herein. The antioxidant system in the topical compositions described herein may be present in a concentration of from any of above 0%, about 0.01 wt %, about 0.05 wt %, about 0.1 wt %, about 0.15 wt %, about 0.2 wt %, about 0.25 wt %, about 0.3 wt %, about 0.35 wt %, or about 0.4 wt % to any of about 0.45 wt %, about 0.5 wt %, about 0.55 wt %, about 0.6 wt %, about 0.65 wt %, about 0.7 wt %, about 0.75 wt %, about 0.8 wt %, about 0.85 wt %, about 0.9 wt %, about 0.95 wt %, or about 1 wt %, based on total weight of the topical composition.

In certain embodiments, the topical composition includes an antioxidant system which includes any of the green tea polyphenols described herein in combination with at least one additional antioxidants.

In one embodiment, the additional antioxidants in the antioxidant system may be selected from the group of cinnamic acid, ferulic acid, caffeic acid, p-coumaric acid, sinapinic acid, cis and trans isomers thereof, salts thereof, equivalent derivatives thereof, and combinations thereof. In another embodiment, the additional antioxidants in the antioxidant system (and in the topical composition generally) may be free or substantially free of cinnamic acid, ferulic acid, caffeic acid, p-coumaric acid, sinapinic acid, cis and trans isomers thereof, salts thereof, equivalent derivatives thereof, and combinations thereof.

In certain embodiments, the additional antioxidants in the antioxidant system may be selected from the group of gallic acid, delphinidin, luteolin, quercetin, cyanidin, taxifolin, kaempferol, malvidin, hesperetin, pelargonidin, apigenin, naringenin, chrysin, ergothioneine, cis and trans isomers thereof, salts thereof, equivalent derivatives thereof, and combinations thereof.

In certain embodiments, the additional antioxidants in the antioxidant system may be selected from the group of apigenin, ergothioneine, cis and trans isomers thereof, salts thereof, equivalent derivatives thereof, and combinations thereof.

Each of the antioxidants in the antioxidant system may be present, individually or cumulatively, in a concentration of from any of above 0 wt %, about 0.01 wt %, about 0.05 wt %, about 0.1 wt %, about 0.15 wt %, about 0.2 wt %, about 0.25 wt %, about 0.3 wt %, about 0.35 wt %, or about 0.4 wt % to any of about 0.45 wt %, about 0.5 wt %, about 0.55 wt %, about 0.6 wt %, about 0.65 wt %, about 0.7 wt %, about 0.75 wt %, about 0.8 wt %, about 0.85 wt %, about 0.9 wt %, about 0.95 wt %, or about 1 wt %, based on total weight of the topical composition.

In certain embodiments, the antioxidant system includes green tea polyphenols in an amount ranging from above 0 wt % to about 0.5 wt %, from above 0 wt % to about 0.1 wt %, or from above 0 wt % to about 0.01 wt %, based on total weight of the topical composition.

In some embodiments, the topical composition incudes an azelaic acid source. The azelaic acid source may be azelogicina.

In some embodiments, the topical composition includes an adaptogen source. The adaptogen source may include Resurgent Power BCR.

In some embodiments, the topical composition further includes one or more of a solvent, a thickener, a chelating agent, vitamin D, a solubilizer, melatonin, preservative, at least one botanical extract, or a colorant.

Suitable solvents that may be used in the topical compositions described herein include, without limitations, polysorbate 20, water, alkanediols (e.g., ethylene glycol, propylene glycol, butylene glycol), ethoxylated or propoxylated diglycol, ethanol, propanol, isopropanol, glycerin, methoxyisopropanol, PPG-2 methyl ether, PPG-3 methyl ether, propylene glycol butyl ether, PPG-2 butyl ether, phenoxyisopropanol, butoxyethanol, butoxydiglycol, methoxydiglycol, phenoxyethanol, PPG-3 butyl ether, PPG-2 propyl ether, propylene glycol propyl ether, or dipropylene glycol dimethyl ether, or mixtures thereof.

In certain embodiments, the solvent may be water, glycerin or a combination thereof. In some embodiments, glycerin is included in an amount from about 0 wt %, about 1 wt %, about 2 wt %, about 3 wt %, about 4 wt %, or about 5 wt % to about 7 wt %, about 8 wt %, about 10 wt %, about 12%, about 15 wt %, or about 20 wt % based on total weight of the topical composition.

In certain embodiments a thickener may include a cellulosic thickener, a synthetic polymer thickener, or a combination thereof. The thickener may be included in the topical composition in any of the following of an amount from about 0 wt %, about 0.5 wt %, about 1 wt % to about 2 wt %, about 2.5 wt %, or about 3 wt % based on total weight of the topical composition.

In certain embodiments, a solubilizer may have an HLB greater than 6, preferably an HLB greater than 12. The solubilizer may be included in the topical composition in any of the following amounts of from about 0 wt %, about 1 wt %, about 2 wt %, about 3 wt %, about 4 wt %, or about 5 wt %, to about 6 wt %, about 7 wt %, about 8 wt %, about 9 wt %, or about 10 wt %, based on total weight of the topical composition.

In certain embodiments, a botanical extract may be thyme herb, mulberry extract, willow bark extract, elderberry, *Echinacea*, cucumber base extract, or a combination thereof.

In some embodiments, the botanical extract is thyme herb. The thyme herb is included in an amount from any of about 0 wt %, about 1 wt %, about 2 wt %, about 3 wt %, about 4 wt %, or about 5 wt % to about 6 wt %, about 7 wt %, about 8 wt %, about 9 wt %, or about 10 wt % based on total weight of the topical composition.

In some embodiments, the botanical extract is mulberry extract. The mulberry extract is included in an amount from any of about 0 wt %, about 1 wt %, about 2 wt %, about 3 wt %, about 4 wt %, or about 5 wt % to about 6 wt %, about 7 wt %, about 8 wt %, about 9 wt %, or about 10 wt % based on total weight of the topical composition.

In some embodiments, the botanical extract is elderberry. The elderberry is included in an amount from any of about 0 wt %, about 1 wt %, about 2 wt %, about 3 wt %, about 4 wt %, or about 5 wt % to about 6 wt %, about 7 wt %, about 8 wt %, about 9 wt %, or about 10 wt % based on total weight of the topical composition.

In some embodiments, the botanical extract is willow bark extract. The willow bark extract is included in an amount from any of about 0 wt %, about 1 wt %, about 2 wt %, about 3 wt %, about 4 wt %, or about 5 wt % to about 6 wt %, about 7 wt %, about 8 wt %, about 9 wt %, or about 10 wt % based on total weight of the topical composition.

In certain embodiments, the preservative is phenoxyethanol.

In some embodiments, the topical composition further includes melatonin. Melatonin may be included in an amount of any from about 0.001 wt %, about 0.01 wt %, or about 0.1 wt %, to about 0.5 wt %, about 1 wt %, or about 2 wt % based on total weight of the topical composition.

In some embodiments, the topical composition further includes allantoin. Allantoin may be included in an amount of any from about 0.001 wt %, about 0.01 wt %, or about 0.1 wt %, to about 0.5 wt %, about 1 wt %, or about 2 wt % based on total weight of the topical composition.

In some embodiments, the topical composition further includes DL panthenol. DL panthenol may be included in an amount of any from about 0 wt %, about 1 wt %, or about 2 wt % to about 3 wt %, about 4 wt %, or about 5 wt % based on total weight of the topical composition.

In some embodiments, the topical composition further includes disodium EDTA. Disodium EDTA may be included in an amount from any of about 0 wt %, about 0.001 wt %, about 0.01 wt %, about 0.1 wt % to about 0.5 wt %, about 0.75 w %, about 0.9 wt %, or about 1 wt % based on total weight of the topical composition.

In some embodiments, the topical composition further includes a plant-based growth factor. In some embodiments, the plant-based growth factor may include a plant-based synthetic human epidermal growth factor (EGF), a plant-based synthetic vascular endothelial growth factor (VEGF), a plant-based synthetic transforming growth factor (TGF), a plant-based synthetic insulin growth factor (IGF), or a combination thereof. For example, the plant-based growth factor may be Reneseed®, Epitensive®, Scelleye®, or a combination thereof (as produced by Lipotrue). In some embodiments, the plant-based growth factor may be included in an amount from about 0.1 wt. % to about 10 wt. %, about 0.5 wt. % to about 9 wt. %, about 1 wt. % to about 8 wt. %, about 2 wt. % to about 7 wt. %, about 3 wt. % to about 6 wt. %, about 4 wt. % to about 5 wt. %, or about 1 wt. % to about 2 wt. %, based on a total weight of the topical composition.

In certain embodiments, the topical composition further includes a cosmetically acceptable excipient. Exemplary cosmetically acceptable excipients, include, without limitations, epidermal penetration enhancer, solvent, mild surfactants, oil bodies, emulsifiers, pearlescent waxes, consistency regulators, thickeners, rheology modifiers, suspending agents, chelating agents, preservatives, superfatting agents, stabilizers, polymers, silicone or siloxane compounds, fats, waxes, lecithins, phospholipids, UV photoprotective factors, biogenic active ingredients, additional antioxidants, deodorants, antiperspirants, antidandruff agents, film formers, swelling agents, insect repellents, self-tanning agents, tyrosinase inhibitors, hydrotropes, solubilizers, perfume oils, dyes, zinc oxide, fatty alcohols, esters of fatty acids, adjuvants, Natural or Synthetic Triglycerides Including Glyceryl Esters and Derivatives, hydrocarbon oils, super-fatting agents, polymers, biogenic active ingredients, hydrotropic agents, bacteria-inhibiting agents, colorants, UV screening agents, agents that absorb UV light and provide photo protection to the skin, or combinations thereof. In certain embodiments, the topical composition includes a cosmetically acceptable excipient selected from the group of solvents, emulsifiers, consistency regulators, thickeners, suspending agents, additional antioxidants, preservatives, perfume oils, or a combination thereof. In certain embodiments, the topical composition is free or substantially free of silicone compounds.

In certain embodiments, the cosmetically acceptable excipient includes glycerin in the topical composition in an amount of from about 2 wt % to about 25 wt %, from about 5 wt % to about 15 wt %, or from about 8 wt % to about 12 wt %, based on total weight of the topical composition.

In certain embodiments, the cosmetically acceptable excipient includes water in the topical composition in an amount of from about 5 wt % to about 95 wt %, about 10 wt % to about 95 wt %, about 20 wt % to about 80 wt %, from about 35 wt % to about 70 wt %, or from about 50 wt % to about 60 wt %, based on total weight of the topical composition.

In certain embodiments, the cosmetically acceptable excipient includes a viscosity agent. The viscosity agent may include xanthan gum, such as Keltrol Advanced Performance LAX-T. In certain embodiments, the cosmetically acceptable excipient includes a chelating agent. Suitable chelating agents include, without limitations, disodium ethylenediaminetetraacetic acid (EDTA), diethylenetriaminepentaacetic acid (DTPA), N-(hydroxyethyl)-ethylenediaminetriacetic acid (HEDTA), Tetrasodium Glutamate Diacetate (GLDA), and nitrilotriacetic acid (NTA).

Methods of Use

In some embodiments, the present disclosure is directed to a method of treating a skin of a subject for effects of radical-induced damage. Radical-induced damage may encompass damage from free radicals from sunlight (UVB, UVA, Visible Light), HEV (blue) light, Infrared (IR), pollution, irritants, allergens, and various environmental toxins that are destructive to the skin, for example, by hydrolyzing elastin fibers in the skin and desynthesizing collagen in the lower dermal layers of the skin. Exemplary radical-induced damage that may be treated, prevented, minimized, reduced, or attenuated after administering to a skin of a subject an effective amount of any of the topical compositions described herein includes, without limitations, skin wrinkles, appearance of fine lines, skin roughness, skin sagging, skin firmness, reduction in skin elasticity, age spots, hyperpigmentation, scars, skin surface irregularities, rosacea, acne, psoriasis, reduction in the skin's regenerative and renewal process, weather-beaten appearance, yellowing, redness, dryness, ichthyosis, and other damaging skin conditions.

In certain embodiments, the present disclosure is directed to a method of brightening a skin of a subject by administering to the skin of a subject an effective amount of any of the topical compositions described herein, wherein the skin is brightened after administration of the topical composition.

In certain embodiments, the present disclosure is directed to a method treating a skin of a subject for effects of atmospheric aging by administering to the skin of a subject an effective amount of any of the topical compositions described herein, wherein the skin exhibits reduction or attenuation of effects of atmospheric aging after administration.

In certain embodiment, the present disclosure is directed to a treatment regimen method that includes administering to a skin of a subject that has been subjected to a dermatological procedure an effective amount of any of the topical compositions described herein. Dermatological procedure that may benefit for subsequent (i.e., post procedure) administration of the topical compositions described herein include, without limitations, non-ablative dermatological procedures, chemical peel, micro-abrasion, laser, and the like. In certain embodiments, the dermatological procedure that may benefit for subsequent (i.e., post procedure) administration of the topical compositions described herein include microdermabrasion, intense pulsed light (IPL), or a non-ablative laser procedure. In certain embodiments, the methods described herein further include performing the dermatological procedure after administration of the topical composition and/or before administration of the topical composition, depending on the treatment regimen.

As used herein, the terms "treatment" or "treating" with respect to a skin condition generally mean "having positive effect on a skin condition" and encompass reduction, amelioration, and/or alleviation of at least one symptom of a skin condition, a reduction, amelioration, and/or alleviation in the severity of the skin conditions, or delay, prevention, or inhibition of the progression of the skin condition. Treatment, as used herein, therefore does not require total curing of the condition. A formulation of the present disclosure that is useful for treatment of a skin condition, or a method of treating a skin condition, need only reduce the severity of a skin condition, reduce the severity of symptoms associated therewith, provide improvement to a patient's quality of life, or delay, prevent, or inhibit the onset of one or more symptoms of a skin condition. As used herein, these terms also encompass aesthetic improvements to the skin upon application of the disclosed formulations having a combination of, for example, an ascorbate component and green tea polyphenols.

As used herein, the phrase "effective amount" refers to an amount of a topical composition of the present disclosure, or component thereof, effective to treat a skin condition as noted above, including a range of effects, from a detectable local improvement in an area of topical application to substantial relief of symptoms to an improvement in one or more aesthetic criteria, including, but not limited to, a perceived improvement in damage from free radicals from sunlight (UVB, UVA, Visible Light), HEV (blue) light, Infrared (IR), pollution, irritants, allergens, and various environmental toxins, skin wrinkles, appearance of fine lines, skin roughness, skin sagging, skin firmness, skin elasticity, age spots, hyperpigmentation, scars, skin surface irregularities, rosacea, acne, psoriasis, skin's regenerative and renewal process, weather-beaten appearance, yellowing, redness, dryness, ichthyosis, and other damaging skin conditions.

The effective amount will vary with the particular condition or conditions being treated, the severity of the condition, the duration of the treatment, the specific components of the composition being used, and other factors. In certain embodiments, the topical compositions described herein are suitable for administration by frequent periodic application, such as by a once, twice, thrice or four times daily application or more, e.g., for a duration of at least 1 day, at least 3 days, at least 5 days, at least 7 days, at least 10 days, at least 14 days, at least 21 days, at least 30 days, and so on. Accordingly, in certain embodiments, the methods described herein further include periodically repeating the administration of the topical composition.

In certain embodiments, the topical compositions described herein are suitable for a pre or post procedure administration, such as before or after a dermatological procedure.

In certain embodiments, since the topical composition described herein is an emulsion of an aqueous and an oily phase, the two phases may separate during storage. Accordingly, in certain embodiments, the methods described herein further include shaking the topical composition to uniformly disperse the oily phase within the aqueous phase prior to administration.

Method of Preparation

The instant disclosure is also directed to a method of preparing any of the topical compositions described herein. The method includes producing any of the topical compositions described herein by combining an ascorbate component, above 0 wt % to about 1 wt % of an antioxidant system that includes green tea polyphenols, and optionally at least one cosmetically acceptable excipient.

The topical composition may be formulated into a serum, gel, lotion, cream, pad applied formulation, and the like.

ILLUSTRATIVE EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1

A topical composition in accordance with embodiments described herein was formulated into a serum having the composition described in Table 1 below. The serum was an emulsion of an aqueous phase and an oily phase and had a pH ranging from about 2.5 to about 3.5.

TABLE 1

Serum Composition

| Ingredient | Amount (wt %) |
|---|---|
| Water | 50 wt %-60 wt % |
| Ascorbic Acid | 10 wt %-20 wt % |
| Tetrahexyldecyl Ascorbate | 2 wt %-10 wt % |
| Green Tea Polyphenols | Above 0 wt %-0.01 wt % |
| Apigenin | Above 0 wt %-0.01 wt % |
| Ergothioneine | Above 0 wt %-0.01 wt % |
| Sclerotium Gum | 0.2 wt %-0.8 wt % |
| Disodium EDTA | 0.05 wt %-0.3 wt % |
| Glycerin | 5 wt %-15 wt % |
| Propanediol | 5 wt %-15 wt % |
| Tocopheryl Acetate | 0.5 wt %-2 wt % |
| PEG-7 Olivate | 0.2 wt %-0.8 wt % |
| Lavender Essential Oil | 0.01 wt %-0.3 wt % |
| Chamomile Essential Oil | 0.01 wt %-0.3 wt % |
| Phenoxyethanol | 0.5 wt %-2 wt % |

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example"

or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

Reference throughout this specification to numerical ranges should not be construed as limiting and should be understood as encompassing the outer limits of the range as well as each number and/or narrower range within the enumerated numerical range.

The term "about", when referring to a physical quantity, is to be understood to include measurement errors within, and inclusive of 10%. For example, "about 100° C." should be understood to mean "100±10° C.".

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A topical composition comprising
a vitamin C source;
a copper source;
one or more cannabinoid components;
sodium hyaluronate; and
an adaptogen.

2. The topical composition of claim 1, wherein the vitamin C source comprises ascorbic acid, tetrahexyldecyl ascorbate, or a combination thereof.

3. The topical composition of claim 1, wherein the copper source comprises copper PCA (pyrrolidone carboxylic acid), copper peptide, or a combination thereof.

4. The topical composition of claim 1, wherein the one or more cannabinoid component comprises hemp oil, purified cannabinoid, hemp seed oil, or a combination thereof.

5. The topical composition of claim 1, further comprising an azelaic acid source.

6. The topical composition of claim 5, wherein the azelaic acid source comprises azeloglicina.

7. The topical composition of claim 1, further comprising an antioxidant system comprising green tea polyphenols.

8. The topical composition of claim 1, further comprising one or more of a solvent, a thickener, a chelating agent, vitamin D, a solubilizer, melatonin, preservative, one or more botanical extracts, a colorant, or a combination thereof.

9. The topical composition of claim 1, wherein the vitamin C source is included in an amount from about 0.001 wt. % to about 20 wt. % based on a total weight of the topical composition.

10. The topical composition of claim 1, wherein the copper source is included in an amount from about 0.001 wt. % to about 5 wt. % based on a total weight of the topical composition.

11. The topical composition of claim 1, wherein sodium hyaluronate is included in an amount from about 0.1 wt. % to about 5 wt. % based on a total weight of the topical composition.

12. The topical composition of claim 1, further comprising a solvent, wherein the solvent includes glycerin and water.

13. The topical composition of claim 1, further comprising allantoin.

14. The topical composition of claim 13, wherein allantoin is included in an amount from about 0 wt. % to about 2 wt. % based on a total weight of the topical composition.

15. The topical composition of claim 1, further comprising DL panthenol.

16. The topical composition of claim 1, further comprising disodium EDTA.

17. The topical composition of claim 1, further comprising a plant-based growth factor.

18. A method of treating skin comprising:
administering to the skin a topical composition according to claim 1.

* * * * *